US00PP08514P

United States Patent [19]

Bak et al.

[11] Patent Number: Plant 8,514

[45] Date of Patent: Dec. 21, 1993

[54] GUZMANIA PLANT NAMED LIMBO

[75] Inventors: Gerardus J. Bak, AA Assendelft; Nicolaas D. Steur, JL Oude Niedorp; Elly Bak, ER Rijsenhout, all of Netherlands

[73] Assignee: Corn. Bak B.V., Assendelft, Netherlands

[21] Appl. No.: 956,097

[22] Filed: Oct. 2, 1992

[51] Int. Cl.[5] ..... A01H 5/00

[52] U.S. Cl. ..... Plt./88.8

[58] Field of Search ..... Plt./88.1, 88.6, 88.8

*Primary Examiner*—James R. Feyrer

*Attorney, Agent, or Firm*—Foley & Lardner

[57] ABSTRACT

A new and distinct cultivar of Guzmania plant named 'Limbo', characterized by the combined features of bicolored cream and lilac upper bracts, and bicolored lilac and green scape bracts, superior floral bract production, solid compact growth habit, and long lasting habit.

1 Drawing Sheet

The present invention relates to a new and distinct cultivar of the genus Guzmania, within the family bromeliaceae, and hereinafter referred to by the cultivar named 'Limbo'.

The genus Guzmania comprises over 100 species of evergreen perennials suitable for cultivation in the home or under glass. Guzmania are predominantly epiphytic with a few terrestrial species and are native to the tropics. For the most part the species vary in diamter from 7 or 8 inches to 3 or 4 feet and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight, and during the spring to autumn period the central vase-like part of the leaf rosette is desirably filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the clayx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

The new cultivar 'Limbo' is a product of a planned breeding program and was originated by the inventors from a cross made during such a program in Assendelft, The Netherlands, in 1982. The male or pollen parent was a selection from Guzmania Wittmackii identified by Code No. 62502, and the female or seed parent was a selection from Guzmania lingulata minor, identified by Code No. 62501. The selection comprising the new variety was chosen after commencement of flowering of the progeny in 1985. The new variety was first asexually propagated by off-shoots, and asexual reproduction through established tissue culture techniques started in 1986 at our facilities located in Assendelft, noted above. Tissue culture is the preferred form of asexual reproduction. It has been clearly demonstrated that the combination of characteristics of 'Limbo' are firmly fixed and are retained through successive generations of asexual reproduction.

'Limbo' is particularly characterized by the following:

1. Solid, compact growth habit.
2. Superior floral bract production.
3. Unique bract color. The scape bracts are a greyed purple (lilac) with green tips. The lowest primary bracts are cream (158B) near the stalk, greyed-purple tinging over cream in the intermediate portion, and greyed-purple at the tips or ends. The upper primary bracts are entirely cream except for greyed-purple tips.
4. Its long lasting habit.

The closest comparison cultivar is 'Amaranth', a Guzmania having purple bracts. 'Limbo' is primarily distinguished from 'Amaranth' by Limbo's bicolored more expansive from the main stalk, and its shorter bract inflorescence relative to the total stalk height.

'Limbo' has not been tested under all available environmental conditions. The phenotype may vary somewhat with variations in environmental conditions such as temperature, light intensity, day length and humidity, without, however, any variation in genotype.

The accompanying color photographic drawings show typical characteristics of 'Limbo', with colors being as true as possible with illustrations of this type.

Sheet 1 comprises a perspective view of a full plant with floral bracts.

Sheet 2 is an enlarged side view showing the floral bracts in more detail.

In the following description, color references are made to The Royal Horticultural Society Colour Chart (R.H.S.).

The following traits have been repeatedly observed and in combination distinguish 'Limbo' as a new and distinct cultivar. These observations, measurements and descriptions have been performed under greenhouse conditions in Assendelft, The Netherlands.

I. Plant:

*Form.*—Funnel form rosette.

*Height.*—Approximately 45 cm high when flowering.

*Growth habit.*—Stemless.

*Diameter.*—Approximately 65 cm.

II. Foliage:

*Size of leaf.*—Approximately 35 to 40 cm long and 3.5 cm wide.

*Shape of leaf.*—Linear — lanceolate.

*Surface texture.*—Smooth.

*Variegation.*—None.

*Color.*—Upperside; 147A; Underside; 137B. (color can vary depending on environmental conditions).

III. Bracts:

*Length.*—Scape bracts: Approximately 10 to 20 cm. Primary bracts: Approximately 4 to 10 cm. Floral bracts: Approximately 5.5 cm.

*Width.*—Primary bracts and scape bracts: approximately 3 cm; floral bracts approximately 1.5 cm.

*General shape.*—Lanceolate.

*Texture.*—Smooth.

*Margin.*—Entire.

*Color.*—Scape bracts: R.H.S. 186A; Scape bract-ends: R.H.S. 137B; Lowest primary bracts parts near to the stalk: R.H.S. 158B; Lowest primary bracts middle parts: R.H.S. 186A; Lowest primary bract-ends: R.H.S. 137B; Higher primary bracts: R.H.S. 158B; Higher primary bract-ends: R.H.S. 186A; (The color changes with maturity: The center of the inflorescence before flowering is R.H.S. 160D-161D, and after flowering is R.H.S. 158B).

IV. Flowers:

*borne (stalks).*—Erect.

*Shape of inflorescence.*—Compound.

*Size of inflorescence on stalk.*—Approximately 12 cm.

*Individual petals.*—(Mostly disposed within the floral bracts hidden behind the primary bracts). (1) Length: Approximately 5.5 cm. (2) Width: Approximately 0.5 cm. (3) Quantity: Approximately 80 flowers divided over approximately 12 branches depending on the size of the plant.(4) Color: R.H.S. 155D.

*Time of blooming.*—A fully grown plant can bloom the whole year starting ± 14 weeks after natural induction or induction through treatment with acetylene.

*Duration of blooms.*—Each flower blooms 1 day and the total duration of blooming is about 6 weeks.

V. Reproductive organs:

*Ovaries.*—Superior.

*Stamens.*—6 in number.

VI. Seed characteristics: Sterile hybrid, therefore no fruit or seed.

I claim:

1. A new and distinct cultivar of Guzmania plant named 'Limbo', as illustrated and described.

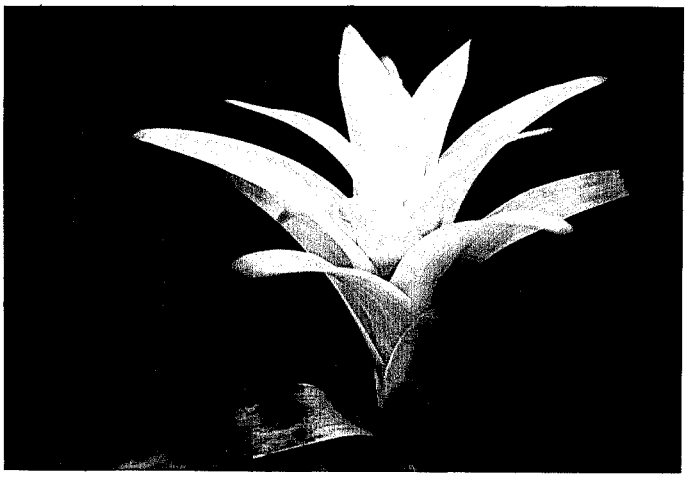
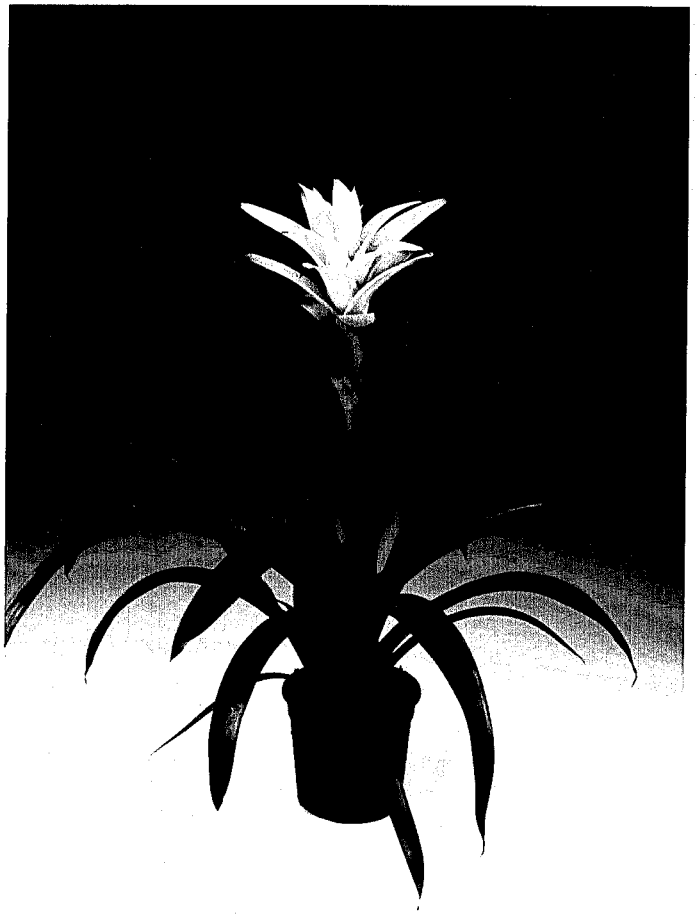

* * * * *